(12) United States Patent
Richard

(10) Patent No.: US 7,919,110 B2
(45) Date of Patent: Apr. 5, 2011

(54) MEDICAL DEVICE DRUG RELEASE REGIONS CONTAINING NON-COVALENTLY BOUND POLYMERS

(75) Inventor: Robert E. Richard, Wrentham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1837 days.

(21) Appl. No.: 11/042,037

(22) Filed: Jan. 25, 2005

(65) Prior Publication Data

US 2006/0165753 A1 Jul. 27, 2006

(51) Int. Cl.
*A61F 2/02* (2006.01)
(52) U.S. Cl. .......................................... 424/425
(58) Field of Classification Search .................. None
See application file for complete search history.

(56) References Cited

U.S. PATENT DOCUMENTS

| 5,840,387 | A | 11/1998 | Berlowitz-Tarrant et al. ............... 428/36.91 |
| 6,071,981 | A | 6/2000 | Johnson et al. ............... 523/105 |
| 6,545,097 | B2 | 4/2003 | Pinchuk et al. ............... 525/240 |
| 2004/0023155 | A1 | 2/2004 | Hayakawa ............... 430/271.1 |
| 2004/0087755 | A1 | 5/2004 | Eling et al. ............... 528/59 |
| 2004/0175406 | A1 | 9/2004 | Schwarz ............... 424/423 |

OTHER PUBLICATIONS

Ranade, Shrirang V. et al., "Physical Characterization of Controlled Release of Paclitaxel fromt he TAXUS™ Express2™ Drug-Eluting Stent", *Journal of Biomedical Materials Research*, vol. 71A (2004): 625-634.
Ranade, Shrirang V. et al., "Styrenic Block Copolymers for Biomaterials and Drug Delivery Applications", *Acta Biomaterialia*, vol. 1 (2005), pp. 137-144.
Binder Wolfgang H. et al., "Supramolecular Poly(ether ketone)-Polyisobutylene Pseudo-Block Copolymers", *Journal of Polymer Science: Part A: Polymer Chemistry*, 2004, vol. 42, pp. 162-172.
Brunsveld, Luc et al., "Supramolecular Polymers," MRS Bulletin, Apr. 2000, pp. 49-53.
Bosman, Anton W., et al., "Supramolecular polymers at work," MaterialsToday, Apr. 2004, pp. 34-39.
Sherrington, David C., et al., "Self-assembly in synthetic macromolecular systems via multiple hydrogen bonding instructions," Chem. Soc. Rev. 2001, vol. 30, pp. 83-93.
Pyun, Jeffrey et al., "Synthesis of Nanocomposite Organic/Inorganic Hybrid Materials using Controlled/"Living" Radical Polymerization," Chem. Mater. 2001, vol. 13, 3436-3448.
Binder, Wolfgang H., et al., "Synthesis and Analysis of Telechelic Polyisobutylenes for Hydrogen-Bonded Supramolecular Pseudo-Block Copolymers," Macromolecules, American Chemical Society, Jul. 2, 2003, revised Dec. 18, 2003, pp. A-K.

*Primary Examiner* — Carlos A Azpuru
(74) *Attorney, Agent, or Firm* — Mayer & Williams PC; David B. Bonham; Keum J. Park

(57) ABSTRACT

According to one aspect, implantable or insertable medical devices are provided, which contain polymeric release regions that release one or more therapeutic agents. The polymeric release regions, in turn, contain the following: (i) a first bonding polymer having a first polymer block and a first bonding group and (ii) a second bonding polymer having a second polymer block and a second bonding group. A therapeutic agent is disposed beneath or within the polymeric release region. The first and second polymer blocks can be the same as or different from one another, as can the first and second bonding groups. The first and second bonding groups are bound to one another via non-covalent bonding, for example, via electrostatic interaction, coordinative bonds, π-π stacking, or hydrogen bonding. According to another aspect, implantable or insertable medical devices are provided, which have a polymeric region that comprises (a) a first polymer having a first polymer block and a first bonding group and (b) a therapeutic agent having a bonding group that bonds to said first bonding group via non-covalent bonding at ambient temperature.

34 Claims, No Drawings

MEDICAL DEVICE DRUG RELEASE REGIONS CONTAINING NON-COVALENTLY BOUND POLYMERS

FIELD OF THE INVENTION

The present invention relates generally to medical devices, and more particularly to medical devices which contain polymer regions for release of therapeutic agents.

BACKGROUND OF THE INVENTION

The in vivo delivery of a biologically active agent within the body of a patient is common in the practice of modern medicine. In vivo delivery of biologically active agents is often implemented using medical devices that may be temporarily or permanently placed at a target site within the body. These medical devices can be maintained, as required, at their target sites for short or prolonged periods of time, delivering biologically active agents at the target site.

For example, numerous polymer-based medical devices have been developed for the delivery of therapeutic agents to the body. Examples include drug eluting coronary stents, which are commercially available from Boston Scientific Corp. (TAXUS), Johnson & Johnson (CYPHER), and others.

In accordance with typical delivery strategies, a therapeutic agent is provided within or beneath a biostable or biodisintegrable polymeric layer that is associated with a medical device. Once the medical device is placed at the desired location within a patient, the therapeutic agent is released from the medical device with a profile that is dependent, for example, upon the loading of the therapeutic agent and upon the nature of the polymeric layer.

Controlling the rate of therapeutic agent release and the overall dose are key parameters for proper treatment in many cases. Selection of the polymeric layer will have a great impact on these parameters. Hence, the ability to tailor the polymeric constituents within the layer, along the interactions between them, is of great interest.

SUMMARY OF THE INVENTION

According to an aspect of the present invention, implantable or insertable medical devices are provided, which contain polymeric release regions that release one or more therapeutic agents. The polymeric release regions, in turn, contain the following: (i) a first bonding polymer comprising a first polymer block and a first bonding group and (ii) a second bonding polymer comprising a second polymer block and a second bonding group. A therapeutic agent is disposed beneath or within the polymeric release region. The first and second polymer blocks can be the same as or different from one another, as can the first and second bonding groups. The first and second bonding groups are bound to one another via non-covalent bonding, for example, via electrostatic interaction, coordinative bonds, π-π stacking, or hydrogen bonding.

Another aspect of the present invention provides an implantable or insertable medical device that contains a polymeric region, which in turn contains (a) a bonding polymer comprising a polymer block and a first bonding group and (b) a therapeutic agent comprising a second bonding group. As above, the first and second bonding groups bond to one another via non-covalent bonding at ambient temperature and are the same or different.

An advantage of the present invention is that polymeric release regions can be provided in which polymers and the interactions between them can be readily tailored to modulate the rate of therapeutic agent release.

These and other embodiments and advantages of the present invention will become immediately apparent to those of ordinary skill in the art upon review of the Detailed Description and Claims to follow.

DETAILED DESCRIPTION OF THE INVENTION

A more complete understanding of the present invention is available by reference to the following detailed description of numerous aspects and embodiments of the invention. The detailed description of the invention which follows is intended to illustrate but not limit the invention. The scope of the invention is defined by the claims.

In one aspect, the present invention provides implantable or insertable medical devices, which contain polymeric release regions, for the release of one or more therapeutic agents. The polymeric release regions contain the following: (i) a first bonding polymer comprising a first polymer block and a first bonding group and (ii) a second bonding polymer comprising a second polymer block and a second bonding group. A therapeutic agent is disposed beneath or within the polymeric release region. The first and second polymer blocks can be the same as, or different from, one another, as can the first and second bonding groups. The first and second bonding groups bond to one another via non-covalent bonding. Various polymer blocks and bonding groups are discussed in more detail below.

As used herein a "release region" is a region that that controls the release of one or more therapeutic agents. A "polymeric region" is a region that comprises polymers, typically at least 50 wt % polymers, at least 75 wt % polymers, at least 90 wt % polymers, or more.

Examples of medical devices to which the present invention is applicable include a wide variety of implantable or insertable medical devices, for example, catheters (e.g., renal or vascular catheters such as balloon catheters), guide wires, balloons, filters (e.g., vena cava filters), stents (including coronary artery stents, peripheral vascular stents such as cerebral stents, urethral stents, ureteral stents, biliary stents, tracheal stents, gastrointestinal stents and esophageal stents), stent grafts, embolic materials and devices including cerebral aneurysm filler coils (including Guglilmi detachable coils and metal coils), vascular grafts, vascular access ports, myocardial plugs, pacemaker leads, left ventricular assist hearts and pumps, total artificial hearts, heart valves, vascular valves, tissue engineering scaffolds for cartilage, bone, skin and other in vivo tissue regeneration, sutures, suture anchors, anastomosis clips and rings, tissue staples and ligating clips at surgical sites, cannulae, metal wire ligatures, orthopedic prosthesis such as bone grafts, bone plates, joint prostheses, orthopedic fixation devices such as interference screws in the ankle, knee, and hand areas, tacks for ligament attachment and meniscal repair, rods and pins for fracture fixation, screws and plates for craniomaxillofacial repair; dental devices such as void fillers following tooth extraction and guided-tissue-regeneration membrane films following periodontal surgery, tissue bulking devices, and tissue engineering scaffolds for cartilage, bone, skin and other in vivo tissue regeneration, as well as various other medical devices that are adapted for implantation or insertion into the body.

The medical devices of the present invention include implantable and insertable medical devices that are used for systemic treatment, as well as those that are used for the localized treatment of any mammalian tissue or organ. Non-limiting examples are tumors; organs including the heart, coronary and peripheral vascular system (referred to overall as "the vasculature"), the urogenital system, including kidneys, bladder, urethra, ureters, prostate, vagina, uterus and ovaries, eyes, lungs, trachea, esophagus, intestines, stomach, brain, liver and pancreas, skeletal muscle, smooth muscle, breast, dermal tissue, cartilage, tooth and bone.

As used herein, "treatment" refers to the prevention of a disease or condition, the reduction or elimination of symptoms associated with a disease or condition, or the substantial or complete elimination of a disease or condition. Preferred subjects (also referred to as "patients") are vertebrate subjects, more preferably mammalian subjects and more preferably human subjects.

Specific examples of medical devices for use in conjunction with the present invention include vascular stents, such as coronary stents and cerebral stents, which deliver a therapeutic agent into the vasculature for the treatment of restenosis.

In some embodiments, the polymeric release regions of the present invention correspond to an entire medical device. In other embodiments, the polymeric release regions correspond or to one or more portions of a medical device. For instance, the polymeric release regions can be in the form of one or more fibers which are incorporated into a medical device, in the form of one or more polymeric layers formed over all or only a portion of an underlying medical device substrate, and so forth. Layers can be provided over an underlying substrate at a variety of locations, and in a variety of shapes, and they can be formed from a variety of polymeric materials. Materials for use as underlying medical device substrates include ceramic, metallic and polymeric substrates. The substrate material can also be a carbon- or silicon-based material. As used herein a "layer" of a given material is a region of that material whose thickness is small compared to both its length and width. As used herein a layer need not be planar, for example, taking on the contours of an underlying substrate. Layers can be discontinuous (e.g., patterned). Terms such as "film," "layer" and "coating" may be used interchangeably herein.

Release regions in accordance with the present invention include carrier regions and barrier regions. By "carrier region" is meant a release region which further comprises a therapeutic agent and from which the therapeutic agent is released. For example, in some embodiments, the carrier region constitutes the entirety of the medical device (e.g., provided in the form of a stent body). In other embodiments, the carrier region corresponds on only a portion of the device (e.g., e.g., a coating overlying a medical device substrate such as a stent body). By "barrier region" is meant a region which is disposed between a source of therapeutic agent and a site of intended release, and which controls the rate at which therapeutic agent is released. For example, in some embodiments, the medical device consists of a barrier region that surrounds a source of therapeutic agent. In other embodiments, the barrier region is disposed over a source of therapeutic agent, which is in turn disposed over all or a portion of a medical device substrate.

In addition to changing the chemical composition of the polymeric release regions, release profile can be modified by changing the size, number or position of the polymeric release regions within the device. For example, the release profile of polymeric carrier and barrier layers in accordance with the presenting invention can be modified by varying the thickness or surface areas of the same. Moreover, multiple polymeric release regions can be employed to modify the release profile. For example, multiple carrier or barrier layers of the invention, either having the same or different content (e.g., different polymeric and/or therapeutic agent content), can be stacked on top of one another, can be positioned laterally to one another, and so forth.

As indicated above, in one aspect, the polymeric release regions for use in the medical devices of the present invention contain first and second bonding polymers, which contain (a) first and second polymer blocks, which can be the same or different, and (b) first and second bonding groups, which can also be the same or different. The first and second bonding groups bond to one another via non-covalent bonding.

Bonding groups for use in the present invention are those groups that bond to one another via non-covalent interactions that are sufficiently strong to allow the polymers to bond together (sometimes referred to as self-assembly) at room temperature. Examples of bonding groups therefore include those that bond via electrostatic interactions, coordinative bonds (e.g., metal-ligand bonding), π-π stacking, and hydrogen bonding, among others.

Hydrogen bonding is particularly suitable for bonding in various aspects of the present invention. In general, for appreciable hydrogen bonding to occur, a hydrogen atom must be attached to a strongly electronegative atom such as O, N, S or P, among others, which is called the hydrogen-bond donor. Without wishing to be bound by theory, it is believed that this electronegative element attracts the electron cloud from around the hydrogen nucleus and leaves the atom with a partial positive charge. Because of the small size of hydrogen relative to other atoms and molecules, the resulting charge, though only partial, nevertheless has a large charge density. A hydrogen bond results when this partial positive charge attracts a lone pair of electrons on another strongly electronegative atom, which is called the hydrogen-bond acceptor.

Typically, the bonding groups used herein are those which provide two, three, four, five, or more hydrogen bonds. Multiple hydrogen bonds commonly occur between bonding groups that contain one or more heterocyclic entities (e.g., monocyclic, bicyclic, tricyclic, etc., entities whose rings are formed from carbon and one or more additional atoms other than carbon, such as O, N, S or P, or other strongly electronegative atoms). Several of these entities are described below.

Various molecules are known which can hydrogen bond with themselves or with complementary molecules. Several examples of such molecules are described in Sherrington D C and Taskinen K A, "Self-assembly in synthetic macromolecular systems via multiple hydrogen bonding interactions," Chem. Soc. Rev., 2001, 30 (2), 83-93, the entire disclosure of which is incorporated by reference.

One example of a molecule that is capable of self-assembly via two hydrogen bonds is 2-acrylamidopyridine

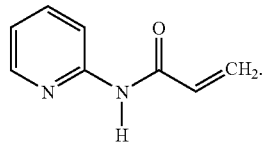

Note that this molecule contains terminal unsaturation, which can be employed in various polymerization reactions, such as those described below, to incorporate it into a bonding polymer. In one specific example, two polymers, designated polymer and polymer' (which designations also include linking molecules, if any) are provided with amidopyridine groups, which have a tendency to self assemble in the following fashion

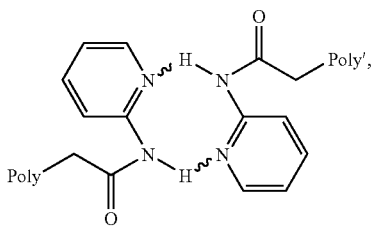

where the two hydrogen bonds are illustrated using zigzag lines. Although bonding between polymer and polymer' ("polymer-polymer' bonding") is shown, because polymer and polymer' have the same bonding groups, polymer-polymer and polymer'-polymer' bonding will also be promoted.

By providing the two polymers (e.g., polymer and polymer') with differing bonding groups, on the other hand, polymer-polymer' bonding is favored. Taking a cue from DNA, one example of such a bonding group pair is based on thymine and adenine, for example,

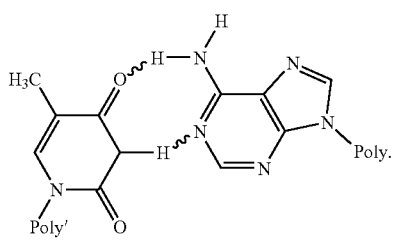

Various bonding groups are also known that pair via three hydrogen bonds. One example is pairing between cytosine and guanine, which may be employed, for example, as follows:

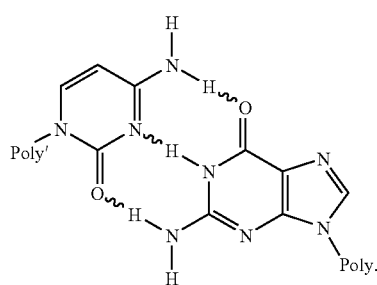

Another example is bonding based on cyanuric acid

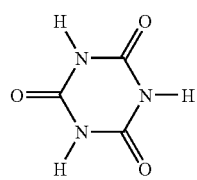

and melamine

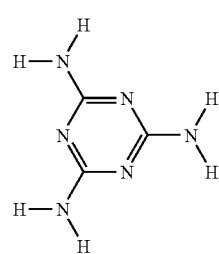

residues, for example,

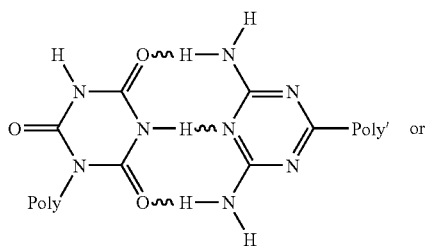

or

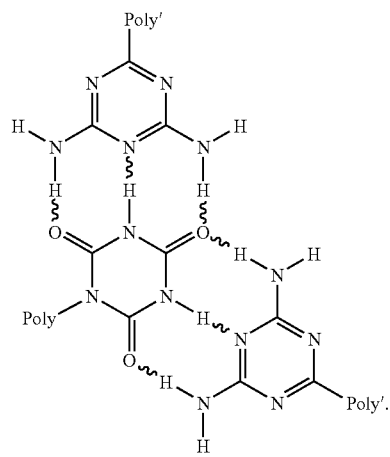

Another example is bonding based on bis(acetylamino) triazine and thymine residues, for example:

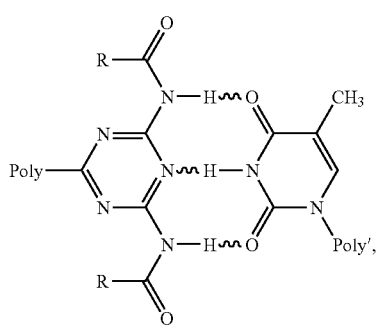

where R is lower alkyl, preferably methyl.

Still other examples involve bonding based on polymers containing melamine and succinimide residues, for instance,

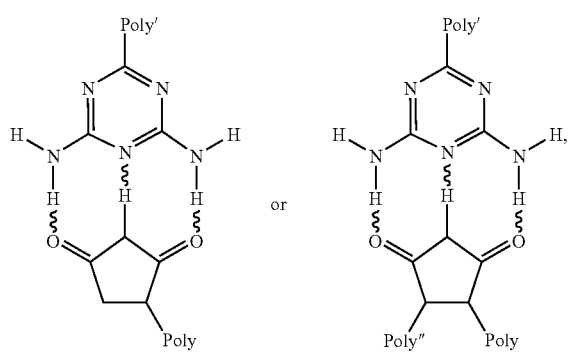

in which the succinimide moiety is shown linked to two different polymers, poly and poly", in the second instance, and bonding based on polymers having melamine and glutarimide residues

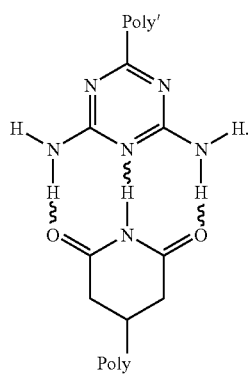

Groups are also known that bind via four or more hydrogen bonds. An example of polymers that bind via four hydrogen bonds are those that bind using uredopyrimidinone residues, for example,

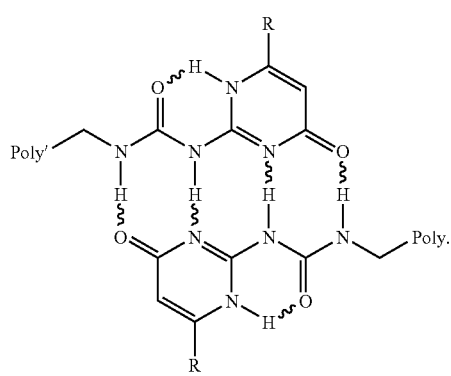

Another example is polymer binding based on the following:

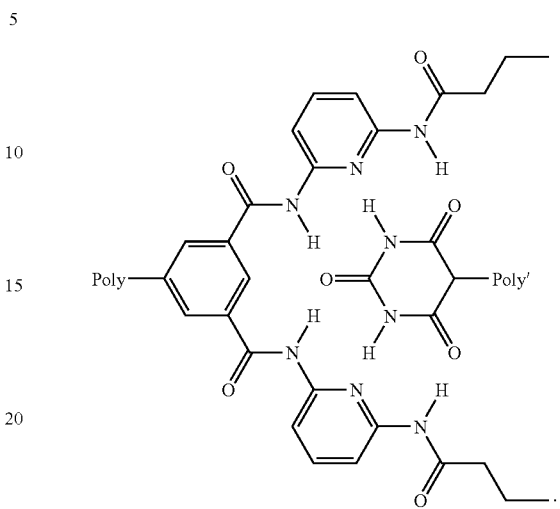

This type of bonding, with several others, is reported in W H Binder et al., "Synthesis and Analysis of Telechelic Polyisobutylenes for Hydrogen-Bonded Supramolecular Pseudo-Block Copolymers," *Macromolecules*, 2004, 37, 1749, the entire disclosure of which is incorporated by reference.

Multiple hydrogen bonds between polymers can also be provided by utilizing multiple bonding groups on a single polymer molecule. Specific examples include, for instance, bonding based on (a) groups which form two hydrogen bonds (e.g., two adjacent thymine-adenine pairs), (b) groups that form two and three hydrogen bonds (e.g., a thymine-adenine pair adjacent a cytosine-guanine pair), (c) groups which form three hydrogen bonds (e.g., two adjacent cytosine-guanine pairs), and so forth.

Bonding groups (e.g., bonding groups utilizing electrostatic interactions, coordinative bonds, π-π stacking, hydrogen bonding, and so forth) can be covalently attached to a wide range of polymer blocks for use in the polymeric release regions of the present invention.

As used herein, "polymers" are molecules that contain one or more chains, each containing multiple copies of the same or differing constitutional units, commonly referred to as monomers. An example of a common polymer chain is polystyrene

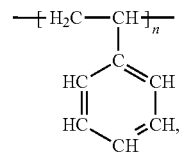

where n is an integer, typically an integer of 10 or more, more typically on the order of 10's, 100's, 1000's or even more, in which the chain contains styrene monomers:

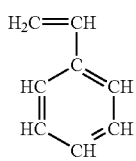

(i.e., the chain originates from, or has the appearance of originating from, the polymerization of styrene monomers, in this case, the addition polymerization of styrene monomers).

A polymer "block", refers to a grouping of 10 or more constitutional units, commonly 20 or more, 50 or more, 100 or more, 200 or more, 500 or more, or even 1000 or more units.

A "chain" is an unbranched monomer grouping.

As used herein, "homopolymer blocks" are polymer blocks whose chains all contain multiple copies of a single constitutional unit. "Copolymer blocks" are polymer blocks, whose chains contain multiple copies of at least two dissimilar constitutional units. Examples of copolymer blocks include random copolymer blocks, statistical copolymer blocks, gradient copolymer blocks, and periodic copolymer blocks (e.g., alternating copolymer blocks).

Polymer blocks for use in the polymeric release regions of the present invention include biostable and biodisintegrable polymer blocks. By "biodisintegrable polymer block" is meant that the polymer undergoes degradation (i.e., bond cleavage, such as hydrolysis), resorption, and/or other disintegration process during the time over which the medical device is designed to reside in the body, which can be on the order of months or even years. By "biostable polymer block" is meant that the polymer block remains substantially intact during the time over which the medical device is designed to reside in the body.

Polymer blocks for use in the polymeric release regions of the present invention can have a variety of architectures, including cyclic, linear and branched architectures. Branched architectures include star-shaped architectures (e.g., architectures in which three or more chains emanate from a single branch point), comb architectures (e.g., architectures having a main chain and a plurality of side chains) and dendritic architectures (e.g., arborescent and hyperbranched polymers), among others.

As noted above, the polymer blocks within the bonding polymers for use in the release regions of the invention can be the same or different. In saying that two polymer blocks are "different," one or more of the following is meant: (a) one polymer block contains a monomer constituent that is not found in the other polymer block, (c) the two polymer blocks have different architectures (e.g., linear vs. branched) and (c) for copolymer blocks, one polymer block has a comonomer distribution that is different from the other (e.g., random vs. alternating). Polymer blocks that differ only by molecular weight are not "different" as the term is used herein.

Polymer blocks for use in conjunction with the present invention can be formed using a wide array of monomers, several of which are listed below. The monomers described below are organized according to the published glass transition temperature ($T_g$) of the corresponding homopolymer, although other organizational schemes could, of course, have been employed. $T_g$ can be measured by any of a number of techniques including differential scanning calorimetry (DSC), dynamic mechanical analysis (DMA), or dielectric analysis (DEA).

A "low $T_g$ polymer block" is a polymer block that displays at least one glass transition temperature that is below ambient temperature, more typically below about 25° C., below about 0° C., below about −25° C., or even below about −50° C. "Ambient temperature" is typically 25° C.-45° C., more typically body temperature (e.g., 35° C.-40° C.). As a result of their low glass transition temperature, low $T_g$ polymer blocks are commonly elastomeric at ambient temperature, although some low $T_g$ polymer blocks, such as silicone (e.g. polydimethylsiloxane), are viscous liquids or millable gums at room temperature.

Monomers that display a low $T_g$ when in homopolymer form include acrylic monomers, methacrylic monomers, vinyl ether monomers, cyclic ether monomers, ester monomers, unsaturated hydrocarbon monomers (including alkene monomers), halogenated unsaturated hydrocarbon monomers (including halogenated alkene monomers), and siloxane monomers. Numerous specific examples are listed below.

Specific acrylic monomers include, for example, (a) alkyl acrylates such as methyl acrylate ($T_g$ 10° C.), ethyl acrylate ($T_g$ −24° C.), propyl acrylate, isopropyl acrylate ($T_g$ −11° C., isotactic), butyl acrylate ($T_g$ −54° C.), sec-butyl acrylate ($T_g$ −26° C.), isobutyl acrylate ($T_g$ −24° C.), cyclohexyl acrylate ($T_g$ 19° C.), 2-ethylhexyl acrylate ($T_g$ −50° C.), dodecyl acrylate ($T_g$ −3° C.) and hexadecyl acrylate ($T_g$ 35° C.), (b) arylalkyl acrylates such as benzyl acrylate ($T_g$ 6° C.), (c) alkoxyalkyl acrylates such as 2-ethoxyethyl acrylate ($T_g$ −50° C.) and 2-methoxyethyl acrylate ($T_g$ −50° C.), (d) halo-alkyl acrylates such as 2,2,2-trifluoroethyl acrylate ($T_g$ −10° C.) and (e) cyano-alkyl acrylates such as 2-cyanoethyl acrylate ($T_g$ 4° C.).

Specific methacrylic monomers include, for example, (a) alkyl methacrylates such as butyl methacrylate ($T_g$ 20° C.), hexyl methacrylate ($T_g$ −5° C.), 2-ethylhexyl methacrylate ($T_g$ −10° C.), octyl methacrylate ($T_g$ −20° C.), dodecyl methacrylate ($T_g$ −65° C.), hexadecyl methacrylate ($T_g$ 15° C.) and octadecyl methacrylate ($T_g$ −100° C.) and (b) aminoalkyl methacrylates such as diethylaminoethyl methacrylate ($T_g$ 20° C.) and 2-tert-butyl-aminoethyl methacrylate ($T_g$ 33° C.).

Specific vinyl ether monomers include for example, (a) alkyl vinyl ethers such as methyl vinyl ether ($T_g$ −31° C.), ethyl vinyl ether ($T_g$ −43° C.), propyl vinyl ether ($T_g$ −49° C.), butyl vinyl ether ($T_g$ −55° C.), isobutyl vinyl ether ($T_g$ −19° C.), 2-ethylhexyl vinyl ether ($T_g$ −66° C.) and dodecyl vinyl ether ($T_g$ −62° C.).

Specific cyclic ether monomers include for example, tetrahydrofuran ($T_g$ −84° C.), trimethylene oxide ($T_g$ −78° C.), ethylene oxide ($T_g$ −66° C.), propylene oxide ($T_g$ −75° C.), methyl glycidyl ether ($T_g$ −62° C.), butyl glycidyl ether ($T_g$ −79° C.), allyl glycidyl ether ($T_g$ −78° C.), epibromohydrin ($T_g$ −14° C.), epichlorohydrin ($T_g$ −22° C.), 1,2-epoxybutane ($T_g$ −70° C.), 1,2-epoxyoctane ($T_g$ −67° C.) and 1,2-epoxydecane ($T_g$ −70° C.).

Specific ester monomers (other than acrylates and methacrylate esters) include for example, ethylene malonate ($T_g$ −29° C.), vinyl acetate ($T_g$ 30° C.), and vinyl propionate ($T_g$ 10° C.).

Specific alkene monomers include, for example, ethylene, propylene ($T_g$ −8 to −13° C.), isobutylene ($T_g$ −73° C.), transbutene ($T_g$ −24° C.), trans-butadiene ($T_g$ −58° C.), 4-methyl pentene ($T_g$ 29° C.), 1-octene ($T_g$ −63° C.) and other α-olefins, cis-isoprene ($T_g$ −63° C.), and trans-isoprene ($T_g$ −66° C.).

Specific halogenated alkene monomers include vinylidene chloride ($T_g$ −18° C.), vinylidene fluoride ($T_g$ −40° C.), cis-chlorobutadiene ($T_g$ −20° C.), and trans-chlorobutadiene ($T_g$ −40° C.).

Specific siloxane monomers include, for example, dimethylsiloxane ($T_g$ −127° C.), diethylsiloxane, methylethylsiloxane, methylphenylsiloxane ($T_g$ −86° C.), and diphenylsiloxane.

An elevated or "high $T_g$ polymer block" is a polymer block that displays at least one glass transition temperature, as measured by any of a number of techniques including differential scanning calorimetry, dynamic mechanical analysis, or thermomechanical analysis, which is above ambient temperature, more typically more typically above 50° C., above 60° C., above 70° C., above 80° C., above 90° C. or even above 100° C.

Monomers that display a high $T_g$ when in homopolymer form include: vinyl aromatic monomers, other vinyl monomers (besides vinyl aromatic monomers), other aromatic monomers (besides vinyl aromatic monomers), methacrylic monomers, and acrylic monomers.

Vinyl aromatic monomers are those having aromatic and vinyl moieties and include, for example, unsubstituted monomers, vinyl-substituted monomers and ring-substituted monomers. Specific vinyl aromatic monomers include the following: (a) unsubstituted vinyl aromatics, such as atactic styrene ($T_g$ 100° C.), isotactic styrene ($T_g$ 100° C.) and 2-vinyl naphthalene ($T_g$ 151° C.), (b) vinyl substituted aromatics such as α-methyl styrene, (c) ring-substituted vinyl aromatics including (i) ring-alkylated vinyl aromatics such as 3-methylstyrene ($T_g$ 97° C.), 4-methylstyrene ($T_g$ 97° C.), 2,4-dimethylstyrene ($T_g$ 112° C.), 2,5-dimethylstyrene ($T_g$ 143° C.), 3,5-dimethylstyrene ($T_g$ 104° C.), 2,4,6-trimethylstyrene ($T_g$ 162° C.), and 4-tert-butylstyrene ($T_g$ 127° C.), (ii) ring-alkoxylated vinyl aromatics, such as 4-methoxystyrene ($T_g$ 113° C.) and 4-ethoxystyrene ($T_g$ 86° C.), (iii) ring-halogenated vinyl aromatics such as 2-chlorostyrene ($T_g$ 119° C.), 3-chlorostyrene ($T_g$ 90° C.), 4-chlorostyrene ($T_g$ 110° C.), 2,6-dichlorostyrene ($T_g$ 167° C.), 4-bromostyrene ($T_g$ 118° C.) and 4-fluorostyrene ($T_g$ 95° C.) and (iv) ester-substituted vinyl aromatics such as 4-acetoxystyrene ($T_g$ 116° C.).

Specific other vinyl monomers include the following: (a) vinyl alcohol ($T_g$ 85° C.); (b) vinyl esters such as vinyl benzoate ($T_g$ 71° C.), vinyl 4-tert-butyl benzoate ($T_g$ 101° C.), vinyl cyclohexanoate ($T_g$ 76° C.), vinyl pivalate ($T_g$ 86° C.), vinyl trifluoroacetate ($T_g$ 46° C.), vinyl butyral ($T_g$ 49° C.), (c) vinyl amines such as 2-vinyl pyridine ($T_g$ 104° C.), 4-vinyl pyridine ($T_g$ 142° C.), and vinyl carbazole ($T_g$ 227° C.), (d) vinyl halides such as vinyl chloride ($T_g$ 81° C.) and vinyl fluoride ($T_g$ 40° C.); (e) alkyl vinyl ethers such as tert-butyl vinyl ether ($T_g$ 88° C.) and cyclohexyl vinyl ether ($T_g$ 81° C.), and (f) other vinyl compounds such as 1-vinyl-2-pyrrolidone ($T_g$ 54° C.) and vinyl ferrocene ($T_g$ 189° C.).

Specific other aromatic monomers, other than vinyl aromatics, include acenaphthalene ($T_g$ 214° C.) and indene ($T_g$ 85° C.).

Specific methacrylic monomers include (a) methacrylic acid ($T_g$ 228° C.), (b) methacrylic acid salts such as sodium methacrylate ($T_g$ 310° C.), (c) methacrylic acid anhydride ($T_g$ 159° C.), (d) methacrylic acid esters (methacrylates) including (i) alkyl methacrylates such as atactic methyl methacrylate ($T_g$ 105-120° C.), syndiotactic methyl methacrylate ($T_g$ 115° C.), ethyl methacrylate ($T_g$ 65° C.), isopropyl methacrylate ($T_g$ 81° C.), isobutyl methacrylate ($T_g$ 53° C.), t-butyl methacrylate ($T_g$ 118° C.) and cyclohexyl methacrylate ($T_g$ 92° C.), (ii) aromatic methacrylates such as phenyl methacrylate ($T_g$ 110° C.) and including aromatic alkyl methacrylates such as benzyl methacrylate ($T_g$ 54° C.), (iii) hydroxyalkyl methacrylates such as 2-hydroxyethyl methacrylate ($T_g$ 57° C.) and 2-hydroxypropyl methacrylate ($T_g$ 76° C.), (iv) additional methacrylates including isobornyl methacrylate ($T_g$ 110° C.) and trimethylsilyl methacrylate ($T_g$ 68° C.), and (e) other methacrylic-acid derivatives including methacrylonitrile ($T_g$ 120° C.).

Specific acrylic monomers include (a) acrylic acid ($T_g$ 105° C.), its anhydride and salt forms, such as potassium acrylate ($T_g$ 194° C.) and sodium acrylate ($T_g$ 230° C.); (b) certain acrylic acid esters such as tert-butyl acrylate ($T_g$ 43-107° C.), hexyl acrylate ($T_g$ 57° C.) and isobornyl acrylate ($T_g$ 94° C.); (c) acrylic acid amides such as acrylamide ($T_g$ 165° C.), N-isopropylacrylamide ($T_g$ 85-130° C.) and N,N dimethylacrylamide ($T_g$ 89° C.); and (d) other acrylic-acid derivatives including acrylonitrile ($T_g$ 125° C.).

Additional monomers, which are commonly found in biodistintegrable polymers, include alpha-hydroxy acids, such as glycolic acid ($T_g$ 35-40° C.), l-lactic acid ($T_g$ 60-65° C.), d,l-lactic acid ($T_g$ 55-60° C.), caprolactone ($T_g$ 58-63° C.) and dioxanone ($T_g$ −10 to 0° C.), among others. Poly(d,l-lactic acid-co-glycolic acid), a common biodisintegrable copolymer, has a $T_g$ that typically ranges from 45 to 55° C.

As will be appreciated by those of ordinary skill in the art, a wide range of polymer blocks may be synthesized from the above and other monomers, according to a number of known polymerization methods, including anionic, cationic and radical polymerization methods, such as azobis(isobutyronitrile)- or peroxide-initiated polymerizations and controlled/"living" radical polymerizations such as metal-catalyzed atom transfer radical polymerization (ATRP), stable free-radical polymerization (SFRP), nitroxide-mediated processes (NMP), and degenerative transfer (e.g., reversible addition-fragmentation chain transfer (RAFT)) processes, among others. These methods are well-detailed in the literature and are described, for example, in an article by Pyun and Matyjaszewski, "Synthesis of Nanocomposite Organic/Inorganic Hybrid Materials Using Controlled/"Living" Radical Polymerization," *Chem. Mater.*, 13:3436-3448 (2001), the contents of which are incorporated by reference in its entirety.

In certain embodiments, polymer blocks for use in the present invention are selected, at least in part, based on their $T_g$ values. As a specific example, in some instances, bonding polymers having high $T_g$ polymer blocks (which can be, for example, homopolymer blocks or copolymer blocks that are formed from one or more of the above high $T_g$ monomers) and bonding polymers having low $T_g$ blocks (which can be, for example, homopolymer blocks or copolymer blocks that are formed from one or more of the above low $T_g$ monomers) are combined within a polymeric release region. At ambient temperatures, the bonding groups of these polymers bind to each other, forming "pseudo" block copolymers. The block copolymers are "pseudo" block copolymers, because the low $T_g$ polymers are linked to the high $T_g$ polymers via non-covalent interactions. These interactions can be disrupted, for example, by heating the polymers or by dissolving the polymers in a solvent system that disrupts the bonding of the bonding groups. Thus, while the pseudo block copolymers' behavior may approximate that of ordinary block copolymers at room temperature and in a patient (e.g., in forming immiscible rubbery and hard phases within the polymeric release regions), in selected solvent systems or at higher temperatures, for example, those that may be experienced during solvent or thermoplastic processing, the pseudo block copolymers may behave more like a mixture of low and high $T_g$ polymers, due to the non-covalent assembly of the bonding polymers, which is disrupted at higher temperatures.

Block copolymers having low and high $T_g$ polymer blocks are known to possess many interesting physical properties due to the presence of a low $T_g$ phase, which is soft and elastomeric at room (and body) temperature, and a high $T_g$ phase, which is hard at these temperatures. As a specific example, block copolymers of polyisobutylene and polystyrene, for example, polystyrene-polyisobutylene-polystyrene triblock copolymers (SIBS copolymers), described in U.S. Pat. No. 6,545,097 to Pinchuk et al., which is hereby incorporated by reference in its entirety, have proven valuable as release polymers in implantable or insertable drug-releasing medical devices. These copolymers are particularly useful for medical device applications because of their excellent strength, biostability and biocompatibility, particularly within the vasculature. These copolymers exhibit high tensile strength, which frequently ranges from 2,000 to 4,000 psi or more, and resist cracking and other forms of degradation under typical in vivo conditions. Biocompatibility, including vascular compatibility, of these materials has been demonstrated by their tendency to provoke minimal adverse tissue reactions (e.g., as measured by reduced macrophage activity). In addition, these polymers are generally hemocompatible as demonstrated by their ability to minimize thrombotic occlusion of small vessels when applied as a coating on coronary stents.

Within the bonding polymers of the present invention, the bonding groups can be covalently attached to the polymer blocks at a variety of positions, for example, at one or both ends of a linear polymer block, at one or more ends of a branched polymer block, along the backbone of the polymer chain(s) of cyclic, linear and branched polymer blocks, and so forth.

In one specific example, bonding groups are provided at one or both ends of a linear polymer block (e.g., a linear polyisobutylene block), and a complementary bonding group is provided at a single end of another linear polymer block (e.g., a linear polystyrene block). As noted above, where hydrogen bonding is employed, the hydrogen bonds can be provided by a single bonding group (e.g., which may be self-complementary or complementary to another group, preferably the latter) or by multiple adjacent bonding groups on the polymer blocks (e.g., analogous to bonding that occurs between complementary oligonucleotides having two or more adjacent base pairs.) Regardless, when linked together, these bonding polymers form pseudo-block copolymers (e.g., polystyrene-polyisobutylene or polystyrene-polyisobutylene-polystyrene pseudo-block copolymers).

In another specific example, bonding groups are provided at the branch ends of a branched polymer block (e.g., at the ends of a polyisobutylene star), while a complementary bonding group is provided at a single end of a linear polymer block (e.g., linear polystyrene). When linked together, these polymers form a pseudo block copolymer (e.g., one having a polyisobutylene star-shaped core and multiple polystyrene arms).

In yet another specific example, bonding groups are provided along the backbone of a linear polymer block (e.g., along a linear polyolefin backbone), while a complementary bonding group is provided at a single end of a linear polymer block (e.g., linear polystyrene). When linked together, these polymers form a pseudo block copolymer (e.g., one having a polyolefin backbone and multiple polystyrene side chains).

Using similar principles, a near infinite array of pseudo-block copolymers can be assembled. For example, bonding groups can be provided at positions other than those discussed above. Moreover, although polyisobutylene and polystyrene blocks are exemplified above, other polymers blocks can be bonded to one another via the bonding groups, including other homopolymer blocks and copolymer blocks (which may be, for example, random, statistical, gradient, or periodic blocks), which may have the above or other polymer architectures.

As noted above, the medical devices of the present invention contain one or more therapeutic agents. "Drugs," "therapeutic agents," "pharmaceutically active agents," "pharmaceutically active materials," and other related terms may be used interchangeably herein. These terms include genetic therapeutic agents, non-genetic therapeutic agents and cells.

Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) beta-blockers, (u) bARKct inhibitors, (v) phospholamban inhibitors, and (w) Serca 2 gene/protein.

Preferred non-genetic therapeutic agents include paclitaxel, sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, and Serca 2 gene/protein among others.

Exemplary genetic therapeutic agents for use in connection with the present invention include anti-sense DNA and RNA as well as DNA coding for the various proteins (as well as the proteins themselves): (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells for use in connection with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK (D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat.

No. 5,733,925 assigned to NeoRx Corporation, the entire disclosure of which is incorporated by reference.

In some embodiments, the therapeutic agents are provided with bonding groups that are complementary to bonding groups present on one or more polymer blocks, for example, in order to delay or control release of the therapeutic agent. This may be attractive, for example, where more than one therapeutic is being released from the same coating region, or where a "bioactive" therapeutic agent is incorporated to modify the surface properties (e.g., where a sulfonated material is incorporated to provide antithrombogenic or antiinflammatory properties to the surface, where a protein or polypeptide is incorporated to enhance tissue healing, and so forth). In the latter case, this may be easier or more effective than covalently attaching the therapeutic agent to modify the surface properties. Bonding groups (e.g., bonding groups utilizing electrostatic interactions, coordinative bonds, $\pi$-$\pi$ stacking, hydrogen bonding, and so forth) can be covalently attached to a wide range of therapeutic agents for use in the present invention.

A wide range of therapeutic agent loadings can be used in connection with the medical devices of the present invention, with the therapeutically effective amount being readily determined by those of ordinary skill in the art and ultimately depending, for example, upon the condition to be treated, the age, sex and condition of the patient, the nature of the therapeutic agent, the nature of the polymeric release region(s), the nature of the medical device, and so forth.

Numerous techniques are available for forming polymeric release regions in accordance with the present invention.

For example, where the polymeric release region is formed from one or more polymers having thermoplastic characteristics, a variety of standard thermoplastic processing techniques can be used to form the polymeric release region, including compression molding, injection molding, blow molding, spinning, vacuum forming and calendaring, as well as extrusion into sheets, fibers, rods, tubes and other cross-sectional profiles of various lengths. Using these and other thermoplastic processing techniques, entire devices or portions thereof can be made. As noted above, an interesting aspect of non-covalently bonded polymers is that they can disengage from one another when heated, thereby allowing them to undergo thermoplastic processing at moderately low temperatures.

Solvent-based techniques can also be used to form the polymeric release regions of the present invention. Using these techniques, a polymeric release region can be formed by first providing a solution that contains the polymers for forming the release region. The solvent that is ultimately selected will contain one or more solvent species, which are generally selected based on their ability to dissolve the polymers that form the polymeric release region, as well as other factors, including drying rate, surface tension, etc. Generally, several solvents will be tested to see which provides polymeric release regions having the best characteristics. Preferred solvent-based techniques include, but are not limited to, solvent casting techniques, spin coating techniques, web coating techniques, solvent spraying techniques, dipping techniques, techniques involving coating via mechanical suspension including air suspension, ink jet techniques, electrostatic techniques, and combinations of these processes.

In some embodiments of the invention, a polymer melt (where thermoplastic processing is employed) or polymer containing solution (where solvent-based processing is employed) is applied to a substrate to form a polymeric release region. For example, the substrate can correspond to all or a portion of an implantable or insertable medical device to which a polymeric release region is applied. The substrate can also be, for example, a template, such as a mold, from which the polymeric release region is removed after solidification. In other embodiments, for example, extrusion and co-extrusion techniques, one or more polymeric release regions are formed without the aid of a substrate.

In a more specific example, an entire stent body is extruded. In another, a polymer release layer is co-extruded along with an underlying stent body. In another, a polymeric layer is provided on an underlying step body by extruding a coating layer onto a pre-existing stent body. In yet another more specific example, a stent is cast in a mold.

If it is desired to provide one or more therapeutic agents and/or any other optional agents in the polymeric release region, and so long as these agents are stable under processing conditions, then they can be provided within the polymer melt or polymer containing solution and co-processed along with the polymer(s). Alternatively, therapeutic and/or other optional agents can be introduced subsequent to the formation of the polymeric release region. For instance, in some embodiments, the therapeutic and/or other optional agents are dissolved or dispersed within a solvent, and the resulting solution contacted with a previously formed polymeric release region (e.g., using one or more of the application techniques described above, such as dipping, spraying, etc.).

As noted above, barrier layers are formed over a therapeutic-agent-containing region in some embodiments of the invention. In these embodiments, a polymeric barrier region can be formed over a therapeutic-agent-containing region, for example, using one of the solvent based or thermoplastic techniques described above. Alternatively, a previously formed polymeric release region can be applied over a therapeutic agent containing region.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An implantable or insertable medical device for therapeutic agent release comprising:
   (a) a polymeric release region that comprises: (i) a first bonding polymer comprising a first polymer block and a first bonding group and (ii) a second bonding polymer comprising a second polymer block and a second bonding group and
   (b) a therapeutic agent disposed beneath or within said polymeric release region,
   wherein said first and second polymer blocks are the same or different, and wherein said first and second bonding groups bond to one another via multiple hydrogen bonds at ambient temperature and are the same or different.

2. The implantable or insertable medical device of claim 1, wherein said first and second bonding groups are different.

3. The implantable or insertable medical device of claim 1, wherein said first and second bonding groups are the same.

4. The implantable or insertable medical device of claim 1, wherein said first and second bonding groups comprise a heterocyclic ring system.

5. The implantable or insertable medical device of claim 1, wherein said first polymer comprises a plurality of bonding groups.

6. The implantable or insertable medical device of claim 5, wherein said second polymer comprises a plurality of bonding groups.

7. The implantable or insertable medical device of claim 1, wherein said first polymer block is a homopolymer or copolymer block having a glass transition temperature below body temperature.

8. The implantable or insertable medical device of claim 7, wherein said first polymer block comprises monomers selected from acrylic monomers, methacrylic monomers, vinyl ether monomers, cyclic ether monomers, ester monomers, unsaturated hydrocarbon monomers, halogenated unsaturated hydrocarbon monomers, siloxane monomers and combinations thereof.

9. The implantable or insertable medical device of claim 1, wherein said first polymer block is a homopolymer or copolymer block having a glass transition temperature above body temperature.

10. The implantable or insertable medical device of claim 9, wherein said first polymer block comprises monomers selected from vinyl monomers, aromatic monomers, acrylic monomers, methacrylic monomers, and combinations thereof.

11. The implantable or insertable medical device of claim 1, wherein said first polymer block is a homopolymer or copolymer block having a glass transition temperature below body temperature, and wherein said second polymer block is a homopolymer or copolymer block having a glass transition temperature above body temperature.

12. The implantable or insertable medical device of claim 11, wherein said first polymer block is a homopolymer or copolymer block that comprises a monomer selected from low $T_g$ olefin monomers, low $T_g$ alkyl acrylate monomers, low $T_g$ alkyl methacrylate monomers, low $T_g$ vinyl ether monomers, low $T_g$ siloxane monomers and combinations thereof, and wherein said second polymer block is a homopolymer or copolymer block that comprises a monomer selected from high $T_g$ vinyl aromatic monomers, high $T_g$ alkyl acrylate monomers, high $T_g$ alkyl methacrylate monomers, high $T_g$ vinyl ether monomers and combinations thereof.

13. The implantable or insertable medical device of claim 1, wherein said first polymer block is a homopolymer or a copolymer block that comprises an alpha-hydroxy acid monomer.

14. The implantable or insertable medical device of claim 1, wherein said first and second polymer blocks are linear polymer blocks.

15. The implantable or insertable medical device of claim 14, wherein bonding groups are provided at one or both ends of said first and second polymer blocks.

16. The implantable or insertable medical device of claim 14, wherein said bonding groups are provided (a) along the backbone of said first polymer block and (b) at one or both ends of said second polymer block.

17. The implantable or insertable medical device of claim 1, wherein said first polymer block is a branched polymer block and wherein said second polymer block is a linear polymer block.

18. The implantable or insertable medical device of claim 17, wherein bonding groups are provided (a) at one or more ends of said first polymer block and (b) at one or both ends of said second polymer block.

19. The implantable or insertable medical device of claim 1, wherein said medical device is selected from a guide wire, a balloon, a catheter, a vena cava filter, a stent, a stent graft, a vascular graft, a cerebral aneurysm filler coil, a myocardial plug, a heart valve, a vascular valve, and a tissue engineering scaffold.

20. The implantable or insertable medical device of claim 1, wherein said therapeutic agent is disposed beneath said release region.

21. The implantable or insertable medical device of claim 1, wherein said therapeutic agent is disposed within said release region.

22. The implantable or insertable medical device of claim 1, wherein said polymeric release region is in the form of a polymeric layer.

23. The implantable or insertable medical device of claim 22, wherein said polymeric layer is disposed over a substrate.

24. The implantable or insertable medical device of claim 23, wherein said polymeric layer is disposed over a region comprising said therapeutic agent.

25. The implantable or insertable medical device of claim 23, wherein said therapeutic agent is disposed within said polymeric layer.

26. The implantable or insertable medical device of claim 1, wherein said polymeric release region is in the form of a fiber.

27. The implantable or insertable medical device of claim 1, wherein said therapeutic agent is selected from anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

28. The implantable or insertable medical device of claim 25, wherein said therapeutic agent comprises a bonding group that hydrogen bonds to said first bonding group, said second bonding group or both of said first and second bonding groups.

29. An implantable or insertable medical device for therapeutic agent release comprising:
  (a) a polymeric release region that comprises (i) a first bonding polymer comprising a first polymer block having a glass transition temperature below body temperature and a first bonding group and (ii) a second bonding polymer comprising a second polymer block having a glass transition temperature above body temperature and a second bonding group, wherein said first and second bonding groups are different and bond to one another by multiple hydrogen bonds and
  (b) a therapeutic agent disposed beneath or within said polymeric release region.

30. The implantable or insertable medical device of claim 29, wherein said first and second polymer blocks are linear polymer blocks and wherein a first bonding group is provided at each end of said first polymer block and a second bonding group is provided at a single end of said second polymer block.

31. The implantable or insertable medical device of claim 29, wherein the first polymer block is a homopolymer or copolymer block that comprises a monomer selected from low $T_g$ olefin monomers, low $T_g$ alkyl acrylate monomers, low $T_g$ alkyl methacrylate monomers, low $T_g$ vinyl ether monomers, low $T_g$ siloxane monomers and combinations thereof and wherein the second polymer block is a homopolymer or copolymer block that comprises a monomer selected from high $T_g$ vinyl aromatic monomers, high $T_g$ alkyl acrylate monomers, high $T_g$ alkyl methacrylate monomers, high $T_g$ vinyl ether monomers and combinations thereof.

32. The implantable or insertable medical device of claim 29, wherein said a first polymer block is a homopolymer or copolymer block that comprises a monomer selected from low $T_g$ olefin monomers, low $T_g$ alkyl acrylate monomers, and low $T_g$ siloxane monomers and combinations thereof and wherein said second polymer block is a homopolymer or copolymer block that comprises a monomer selected from high $T_g$ vinyl aromatic monomers.

33. The implantable or insertable medical device of claim 29, wherein said medical device is selected from a guide wire, a balloon, a catheter, a vena cava filter, a stent, a stent graft, a vascular graft, a cerebral aneurysm filler coil, a myocardial plug, a heart valve, a vascular valve, and a tissue engineering scaffold.

34. The implantable or insertable medical device of claim 29, wherein said therapeutic agent is disposed within said polymeric release region and wherein said therapeutic agent comprises a bonding group that hydrogen bonds to said first bonding group, said second bonding group, or both of said first and second bonding groups.

* * * * *

UNITED STATES PATENT AND TRADEMARK OFFICE
CERTIFICATE OF CORRECTION

| | | |
|---|---|---|
| PATENT NO. | : 7,919,110 B2 | Page 1 of 1 |
| APPLICATION NO. | : 11/042037 | |
| DATED | : April 5, 2011 | |
| INVENTOR(S) | : Robert E. Richard | |

It is certified that error appears in the above-identified patent and that said Letters Patent is hereby corrected as shown below:

Col. 2, line 30, after "that" remove "that".

Col. 9, line 52, after "block" change "(c)" to --(b)--.

Signed and Sealed this
Twenty-seventh Day of September, 2011

David J. Kappos
*Director of the United States Patent and Trademark Office*